(12) United States Patent
Faught et al.

(10) Patent No.: US 12,194,284 B2
(45) Date of Patent: Jan. 14, 2025

(54) SMART SYRINGE USING NFC COMMUNICATION AND CAPACITANCE DETECTION

(71) Applicant: West Pharmaceutical Services, Inc., Exton, PA (US)

(72) Inventors: Stacy Faught, Scottsdale, AZ (US); Jorge Santos, Scottsdale, AZ (US)

(73) Assignee: West Pharmaceutical Services, Inc., Exton, PA (US)

(*) Notice: Subject to any disclaimer, the term of this patent is extended or adjusted under 35 U.S.C. 154(b) by 1257 days.

(21) Appl. No.: 16/615,991

(22) PCT Filed: May 25, 2018

(86) PCT No.: PCT/US2018/034690
§ 371 (c)(1),
(2) Date: Nov. 22, 2019

(87) PCT Pub. No.: WO2018/218167
PCT Pub. Date: Nov. 29, 2018

(65) Prior Publication Data
US 2020/0139053 A1   May 7, 2020

Related U.S. Application Data

(60) Provisional application No. 62/511,114, filed on May 25, 2017.

(51) Int. Cl.
*A61M 5/20*   (2006.01)
*A61M 5/24*   (2006.01)
(Continued)

(52) U.S. Cl.
CPC ............ *A61M 5/3157* (2013.01); *A61M 5/20* (2013.01); *A61M 5/24* (2013.01);
(Continued)

(58) Field of Classification Search
CPC ........ A61M 5/3157; A61M 5/20; A61M 5/24; A61M 5/31568; A61M 5/178; A61M 2205/3317; A61M 2205/52
See application file for complete search history.

(56) References Cited

U.S. PATENT DOCUMENTS 5,628,309 A   5/1997   Brown
5,658,259 A   8/1997   Pearson
(Continued)

FOREIGN PATENT DOCUMENTS

CN   1229679 A   9/1999
CN   1518463 A   8/2004
(Continued)

OTHER PUBLICATIONS

Int'l Preliminary Report on Patentability issued Sep. 18, 2019 in Int'l Application No. PCT/US2018/034690.
(Continued)

*Primary Examiner* — Nathan R Price
*Assistant Examiner* — Tania Ismail
(74) *Attorney, Agent, or Firm* — Blank Rome LLP

(57) ABSTRACT

A syringe includes a plunger having multiple sections of differing diameters or materials, and a barrel with a cavity into which the plunger is inserted. The barrel includes a first probe and a second probe opposite to one another such that an interior volume of the barrel is radially between the first and second probes. A microcontroller is configured to measure a capacitance between the first and second probes, with the measured capacitance having a first capacitance value when the first section of the plunger shaft is between the first and second probes and a second capacitance value different from the first capacitance value when a second section of the plunger shaft is between the first and second probes. The microcontroller is configured to determine that an injection
(Continued)

has been completed when the second capacitance value is measured.

25 Claims, 8 Drawing Sheets

(51) Int. Cl.
    A61M 5/315     (2006.01)
    A61M 5/178     (2006.01)
    G16H 20/17     (2018.01)
    G16H 40/63     (2018.01)
(52) U.S. Cl.
    CPC ......... A61M 5/31568 (2013.01); A61M 5/178
              (2013.01); A61M 2205/3317 (2013.01); A61M
                        2205/3569 (2013.01); A61M 2205/52
                  (2013.01); G16H 20/17 (2018.01); G16H
                                          40/63 (2018.01)

(56) References Cited

U.S. PATENT DOCUMENTS

| | | | |
|---|---|---|---|
| D387,865 S | 12/1997 | Peckham | |
| 5,720,733 A | 2/1998 | Brown | |
| 5,814,015 A | 9/1998 | Gargano et al. | |
| 6,171,283 B1 | 1/2001 | Perez | |
| 6,270,455 B1* | 8/2001 | Brown | G16H 20/17 |
| | | | 128/920 |
| 6,810,350 B2 | 10/2004 | Blakley | |
| D637,311 S | 5/2011 | Isobe | |
| 8,226,610 B2 | 7/2012 | Edwards | |
| D690,416 S | 9/2013 | Cappello | |
| 8,808,269 B2 | 8/2014 | Bazargan et al. | |
| 8,827,964 B2 | 9/2014 | Boyd | |
| 9,181,008 B2 | 11/2015 | Milan | |
| 9,233,213 B2 | 1/2016 | Olson | |
| 9,278,177 B2 | 3/2016 | Edwards | |
| 9,395,716 B2* | 7/2016 | Bammer | A61M 5/1684 |
| 9,470,587 B1 | 10/2016 | Greene | |
| D805,193 S | 12/2017 | Shoji | |
| D827,132 S | 8/2018 | Jörg | |
| D839,422 S | 1/2019 | Jörg | |
| D847,371 S | 4/2019 | Koseoglu | |
| D870,308 S | 12/2019 | Samarasinha | |
| D881,392 S | 4/2020 | Pujara | |
| D887,578 S | 6/2020 | Koseoglu | |
| D888,945 S | 6/2020 | Yemane-Tekeste | |
| 11,020,529 B2* | 6/2021 | Schabbach | A61M 5/24 |
| 2002/0188419 A1 | 12/2002 | Slate | |
| 2004/0034323 A1 | 2/2004 | Manthey | |
| 2005/0187522 A1 | 8/2005 | Miller | |
| 2006/0161114 A1 | 7/2006 | Perot | |
| 2007/0239116 A1 | 10/2007 | Follman | |
| 2008/0167611 A1 | 7/2008 | Miller | |
| 2008/0300549 A1 | 12/2008 | Verespej | |
| 2008/0312604 A1 | 12/2008 | Boesen | |
| 2009/0024112 A1 | 1/2009 | Edwards | |
| 2009/0030366 A1 | 1/2009 | Hochman | |
| 2009/0105647 A1* | 4/2009 | Rush | F04B 19/22 |
| | | | 604/151 |
| 2009/0318866 A1 | 12/2009 | Ferrari | |
| 2010/0211005 A1 | 8/2010 | Edwards | |
| 2011/0092915 A1 | 4/2011 | Olson | |
| 2013/0184655 A1 | 7/2013 | Lanzi | |
| 2014/0039406 A1 | 2/2014 | Verespej | |
| 2014/0058349 A1 | 2/2014 | Bazargan et al. | |
| 2014/0155827 A1 | 6/2014 | Ostrander | |
| 2014/0276411 A1 | 9/2014 | Cowan et al. | |
| 2015/0011944 A1 | 1/2015 | Young | |
| 2015/0011965 A1 | 1/2015 | Cabiri | |
| 2015/0059901 A1 | 3/2015 | Jin | |
| 2015/0061389 A1 | 3/2015 | Song | |
| 2015/0075520 A1 | 3/2015 | Kakuta | |
| 2015/0080810 A1 | 3/2015 | Henderson | |
| 2015/0165129 A1 | 6/2015 | Row | |
| 2016/0022916 A1* | 1/2016 | Tran | A61M 5/31511 |
| | | | 604/229 |
| 2016/0375195 A1 | 12/2016 | Fabien | |
| 2017/0049973 A1 | 2/2017 | Tieck et al. | |
| 2017/0224934 A1 | 8/2017 | Shultz | |
| 2017/0239427 A1 | 8/2017 | Mehawej | |
| 2017/0348478 A1 | 12/2017 | Tobescu | |
| 2017/0354791 A1 | 12/2017 | Lewkonya | |
| 2018/0147360 A1 | 5/2018 | Kemp | |
| 2018/0243506 A1 | 8/2018 | Niven | |
| 2020/0282152 A1 | 9/2020 | Hezkiahu | |

FOREIGN PATENT DOCUMENTS

| | | |
|---|---|---|
| CN | 201662686 U | 12/2010 |
| CN | 102058918 A | 5/2011 |
| CN | 102413855 A | 4/2012 |
| CN | 102421472 A | 4/2012 |
| CN | 104411351 A | 3/2015 |
| CN | 104470563 A | 3/2015 |
| CN | 205287099 U | 6/2016 |
| CN | 205658923 U | 10/2016 |
| CN | 106470716 A | 3/2017 |
| CN | 106573110 A | 4/2017 |
| EP | 0864335 A2 | 9/1998 |
| EP | 0635277 B1 | 11/2001 |
| EP | 2340415 A2 | 7/2011 |
| EP | 2340415 B1 | 7/2016 |
| EP | 3100754 A1 | 12/2016 |
| JP | H11-500643 A | 1/1999 |
| JP | 2010534552 A | 11/2010 |
| JP | 2012508081 A | 4/2012 |
| JP | 2014516667 A | 7/2014 |
| JP | 2015514518 A | 5/2015 |
| JP | 2017511209 A | 4/2017 |
| RU | 2557896 C2 | 7/2015 |
| WO | 2007107558 A2 | 9/2007 |
| WO | 2010038031 A2 | 4/2010 |
| WO | 2013146000 A1 | 10/2013 |
| WO | 2013159059 A1 | 10/2013 |
| WO | 2014150201 A1 | 9/2014 |
| WO | 2015061389 A1 | 4/2015 |
| WO | 2015157785 A1 | 10/2015 |
| WO | 2016033507 A2 | 3/2016 |
| WO | WO 2016/040949 A1 | 3/2016 |
| WO | 2016166338 A1 | 10/2016 |
| WO | 2016172048 A1 | 10/2016 |
| WO | 2017050781 A1 | 3/2017 |

OTHER PUBLICATIONS

Int'l Search Report and Written Opinion issued Aug. 21, 2018 in Int'l Appliction No. PCT/US2018/034690.
Office Action issued Sep. 8, 2020 in European Application No. 18731686.4.
Office Action issued Nov. 10, 2020 in JP Application No. 2019-564961.
Extended European Search Report dated Aug. 5, 2020 in European Application No. 18780556.9.
Int'l Preliminary Report on Patentability issued Sep. 18, 2019 in Int'l Application No. PCT/US2018/053819.
Int'l Search Report and Written Opinion dated Jul. 12, 2018 in Int'l Application No. PCT/US2018/026556.
Int'l Search Report and Written Opinion issued Jan. 7, 2019 in Int'l Application No. PCT/US2018/053819.
International Preliminary Report on Patentability dated Oct. 8, 2019 in Int'l Application No. PCT/US2018/026556.
Office Action dated Mar. 17, 2020 in JP Application No. 2019-554804.

* cited by examiner

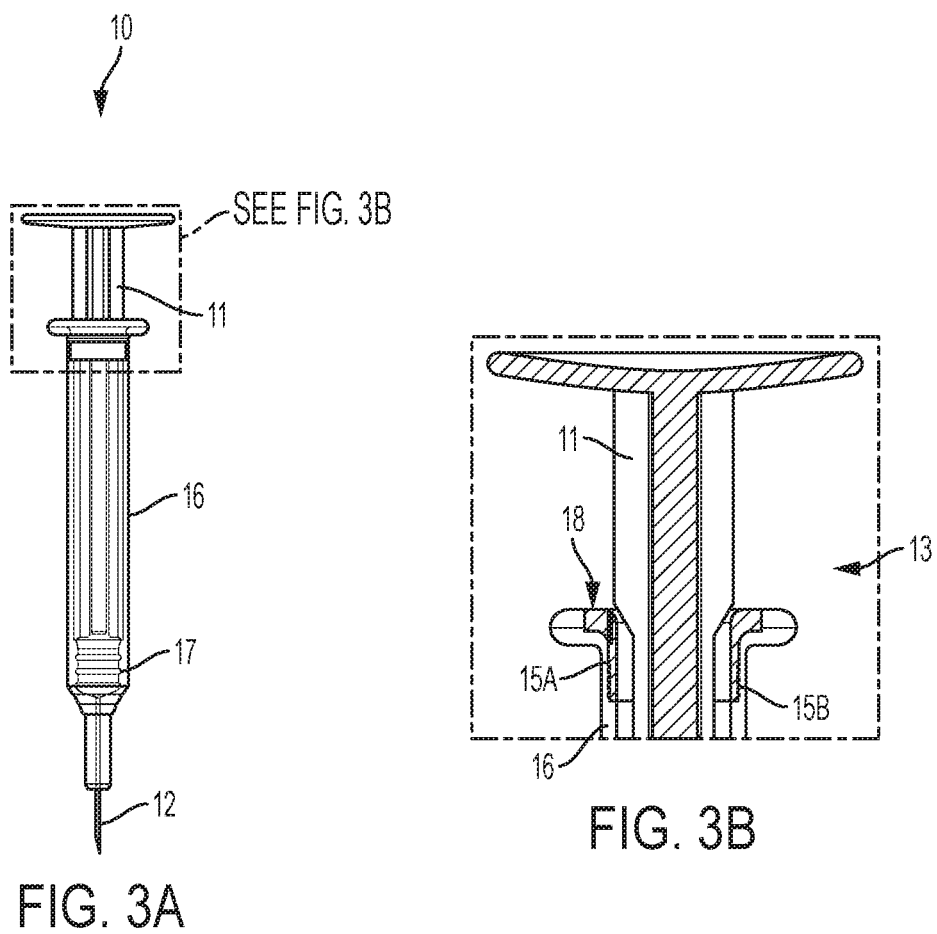

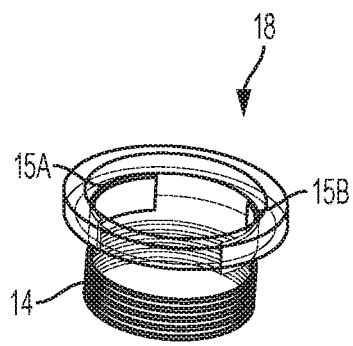
FIG. 5
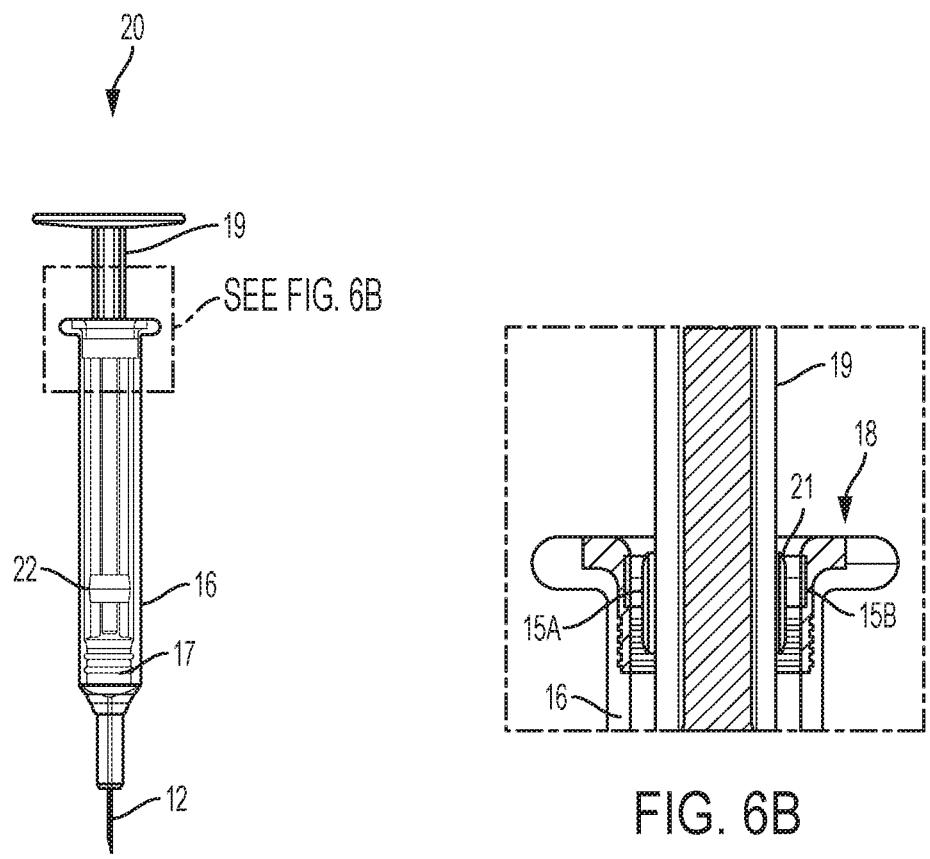
FIG. 6A
FIG. 6B

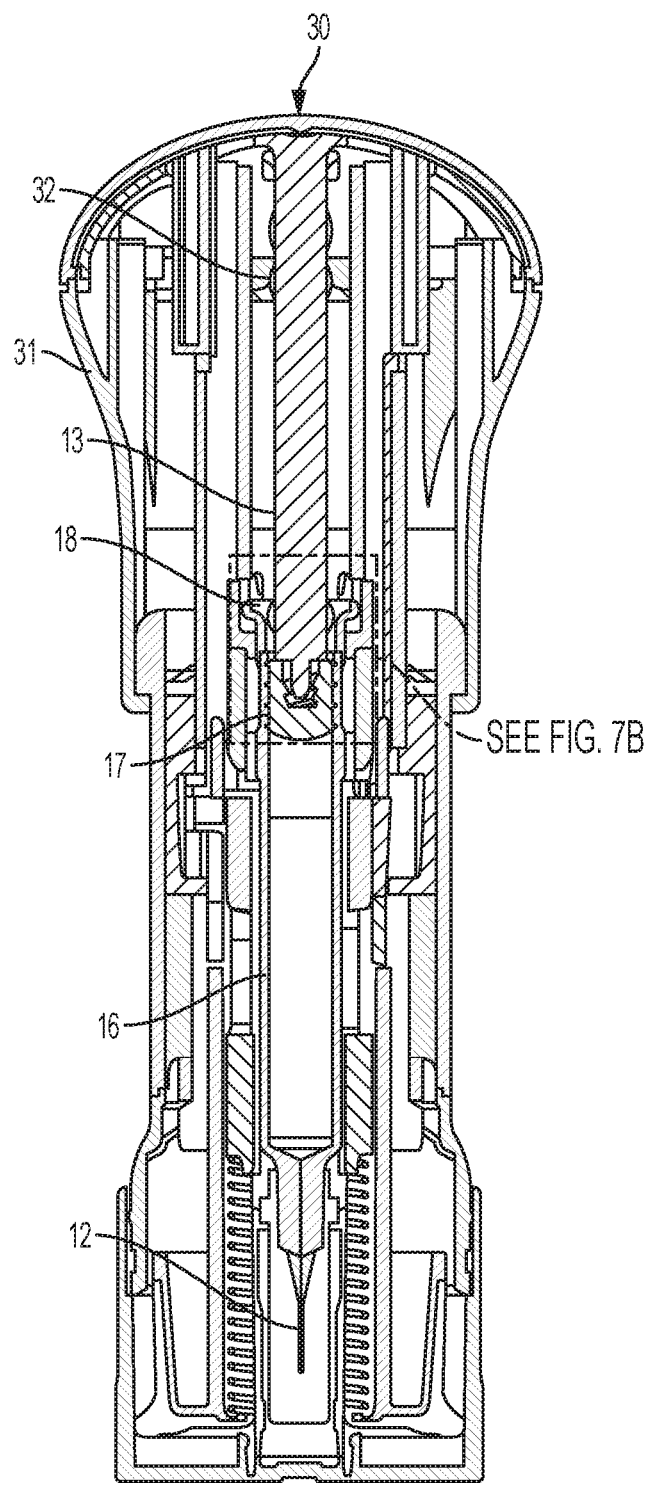
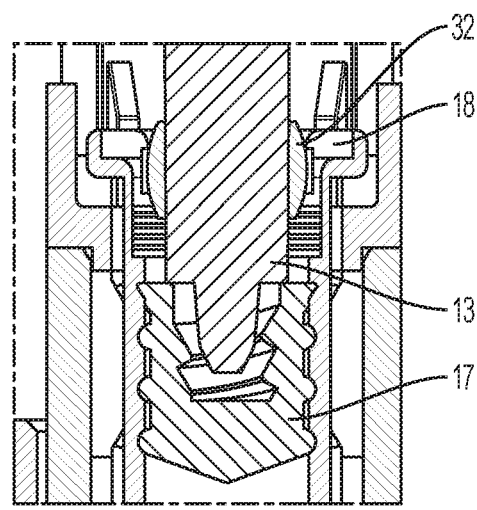
FIG. 7A
FIG. 7B

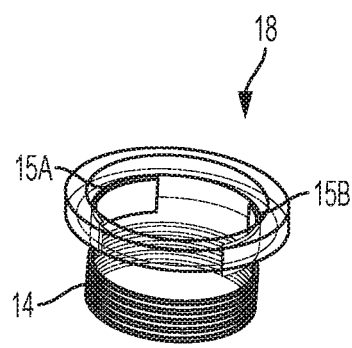
FIG. 8
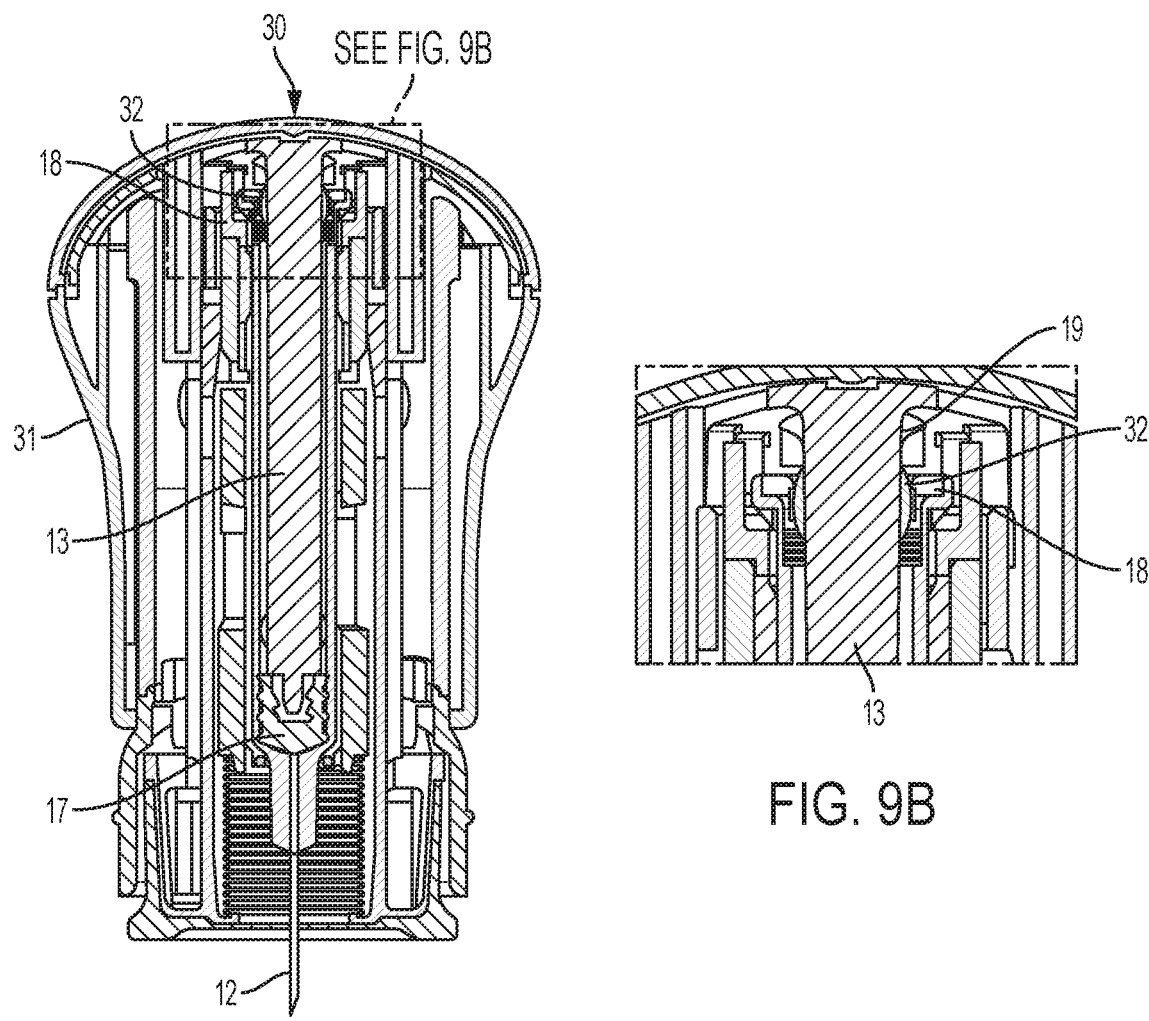
FIG. 9A
FIG. 9B

SMART SYRINGE USING NFC COMMUNICATION AND CAPACITANCE DETECTION

CROSS-REFERENCE TO RELATED APPLICATIONS

This application is a section 371 of International Application No. PCT/US2018/034690, filed May 25, 2018, which was published on Nov. 29, 2018 under International Publication No. WO 2018/218167 A1, and which claims priority to U.S. Provisional Patent Application No. 62/511,114, filed May 25, 2017, the entire contents of each of which are incorporated herein by reference.

BACKGROUND

The need for patient medication adherence has been recognized as a negative driver of cost in the healthcare system. Digital adherence management has been shown to be an effective method to increase the rate of adherence, in particular for patients with chronic diseases, and to decrease the cost and negative health outcomes. Prior efforts in this area were restricted to self-reporting and/or barcode scanning, but these methods are time consuming and still rely on the patient to report the use of their general device without confirmation that it was used correctly, if at all.

Some next-generation devices have begun to solve this problem using batteries and Bluetooth technology, but for low-cost devices, such as prefilled syringes, the communication tool may sometimes cost more than the product itself. An affordable method that can be built into any syringe or container will enable connectivity across nearly every device used to self-inject, from simple syringes to auto-injectors and patch injection systems, by enabling the syringe to contain the technology, rather than the device, and by enabling the detection of a state change of the syringe apart from the device mechanism.

Other products have included some form of Near Field Communication (NFC) technology into the plastic components of an auto-injector or pen injector, but these have been passive solutions, which merely re-direct the user to an instruction for use (IFU) or some other web interface, and do not actively communicate the status of the device (used vs. unused, or the amount of movement of the piston in the syringe or cartridge). Other devices have used battery-powered Bluetooth technology to initiate active communication with another device such as a smartphone, but these devices must contain a battery or some other form of self-power, and the technology to do this comes at a higher cost. Other NFC technologies were passive in nature, and thus were unable to communicate the real-time state of the device. Bluetooth Low Energy (BLE) technologies are relatively expensive and require built-in batteries or some other form of on-board power.

BRIEF SUMMARY

Embodiments can provide a syringe including a plunger having a shaft extending longitudinally between a proximal end and a distal end. The shaft includes a first section having a first diameter, and a second section having a second diameter different from the first diameter. The second section is disposed between the first section and the proximal end of the plunger. The syringe can also include a barrel having a proximal end and a distal end and a cylindrical sidewall extending longitudinally between the proximal and distal ends. The sidewall defines an internal volume, and the distal end of the plunger is inserted into a proximal end of the barrel and is movable within the internal volume with respect to the barrel in the longitudinal direction. A first probe and a second probe are disposed on the barrel adjacent a proximal end of the barrel. The first and second probes can be opposite to one another such that the interior volume of the barrel is radially between the first and second probes. A microcontroller can be disposed on the barrel and in electrical communication with the first and second probes, with the microcontroller being configured to measure a capacitance between the first and second probes. The measured capacitance has a first capacitance value when the first section of the plunger shaft is between the first and second probes and a second capacitance value different from the first capacitance value when the second section of the plunger shaft is between the first and second probes. The microcontroller is also configured to determine that an injection has been completed when the second capacitance value is measured.

Embodiments can further provide a syringe further including a NFC antenna disposed on the barrel and communicatively coupled to the microcontroller. The microcontroller is further configured to transmit data related to the determination that an injection has been completed to an external device via the NFC antenna.

Embodiments can further provide a syringe including a memory disposed on the barrel and configured to store data related to capacitance measurements made by the microcontroller.

Embodiments can further provide a syringe wherein the second diameter is larger than the first diameter.

Embodiments can further provide a syringe wherein at least a portion of each of the plunger and the barrel are enclosed within one of a manual self-injection device or an auto-injection device.

Embodiments can further provide a syringe wherein the first and second probes and the microcontroller are included within an inlay disposed on the barrel.

Embodiments can further provide a syringe wherein the inlay is molded into the barrel.

Embodiments can further provide a syringe including a plunger having a shaft extending longitudinally between a proximal end and a distal end. The shaft can include a first section made from a first material, and a second section made from a second material different from the first material, with the second section being disposed between the first section and the proximal end of the plunger. The syringe can further include a barrel having a proximal end and a distal end and a cylindrical sidewall extending between longitudinally between the proximal and distal ends. The sidewall defines an internal volume, and the distal end of the plunger is inserted into a proximal end of the syringe barrel and is movable within the internal volume with respect to the syringe barrel in the longitudinal direction. The syringe can further include a first probe and a second probe disposed on the barrel adjacent a proximal end of the barrel. The first and second probes are opposite to one another such that the interior volume of the barrel is radially between the first and second probes. Additionally, a microcontroller can be disposed on the barrel and in electrical communication with the first and second probes, with the microcontroller being configured to measure a capacitance between the first and second probes. The measured capacitance has a first capacitance value when the first section of the plunger shaft is between the first and second probes and a second capacitance value different from the first capacitance value when the second section of the plunger shaft is between the first and second probes. The microcontroller is further configured to determine that an injection has been completed when the second capacitance value is measured.

Embodiments can further provide a syringe wherein the plunger further includes a third section made from a third material different from the first and second materials, and the third section is disposed between the first and second sections. The measured capacitance has a third capacitance value different from the first and second capacitance values when the third section is between the first and second probes, and the microcontroller is configured to determine a position of the plunger based on the measured capacitance.

Embodiments can further provide a syringe further including an NFC antenna disposed on the barrel and communicatively coupled to the microcontroller. The microcontroller is further configured to transmit data related to the determination that an injection has been completed to an external device via the NFC antenna.

Embodiments can further provide a syringe further including a memory disposed on the barrel and configured to store data related to capacitance measurements made by the microcontroller.

Embodiments can further provide a syringe wherein at least a portion of each of the plunger and the barrel are enclosed within one of a manual self-injection device or an auto-injection device.

Embodiments can further provide a syringe wherein first and second probes and the microcontroller are included within an inlay disposed on the barrel.

Embodiments can further provide a method of using a syringe having a plunger movably disposed within a barrel. The method includes measuring, by a microcontroller disposed on the barrel, a first capacitance value between first and second probes disposed on the barrel and electrically connected to the microcontroller when a first section of the plunger is disposed between the first and second probes. The method can further include measuring, by the microcontroller, a second capacitance value between the first and second probes when a second section of the plunger different from the first section is disposed between the first and second probes, with the second capacitance value being different from the first capacitance value. The method can further include determining, by the microcontroller, that an injection has been completed when the second capacitance value has been measured.

Embodiments can further provide a method wherein the first section of the plunger has a first diameter and the second section of the plunger has a second diameter different from the first diameter.

Embodiments can further provide a method wherein the first section of the plunger is made from a first material and the second section of the plunger is made from a second material different from the first material.

Embodiments can further provide a method further including transmitting, by the microcontroller via an NFC antenna, data regarding the determination that the injection has been completed to a smart device or a cloud-based server.

Embodiments can further provide a method further including measuring, by the microcontroller, a third capacitance value between the first and second probes when a third section of the plunger between the first and second sections is disposed between the first and second probes, the third capacitance value being different from the first and second capacitance values. The method can further include determining, by the microcontroller, a position of the plunger relative to the barrel based on which of the first, second, and third capacitance values is measured by the microcontroller.

Embodiments can further provide a method further comprising storing, by the microcontroller, data regarding the plunger position in a memory disposed on the barrel.

BRIEF DESCRIPTION OF THE DRAWINGS

Various aspects of the disclosure will now be described in connection with the attached drawings. For the purpose of illustration, there are shown in the drawings embodiments which are presently preferred. It should be understood, however, that the invention is not limited to the precise arrangements and instrumentalities shown.

FIG. 3A is a front side elevational view of the syringe system of FIG. 1A after dispensing medicament;

FIG. 3B is an enlarged, front side elevational cross-sectional view of a portion of the syringe system of FIG. 3A;

FIG. 5 is a perspective view of an inlay for use in the syringe system of FIG. 4A;

FIG. 6A is a front side elevational view of the syringe system of FIG. 4A after dispensing medicament;

FIG. 6B is an enlarged, front side elevational cross-sectional view of a portion of the syringe system of FIG. 6A;

FIG. 7A is a front side elevational cross-sectional view of a syringe system embedded within a manual self-injector in accordance with a third preferred embodiment of the present invention before dispensing medicament contained therein;

FIG. 7B is an enlarged, front side elevational cross-sectional view of a portion of the syringe system and self-injector of FIG. 7A;

FIG. 8 is a perspective view of an inlay for use in the syringe system of FIG. 7A;

FIG. 9A front side elevational cross-sectional view of the syringe system and self-injector of FIG. 7A in a configuration for dispensing medicament;

FIG. 9B is an enlarged, front side elevational cross-sectional view of a portion of the syringe system and self-injector of FIG. 9A;

DETAILED DESCRIPTION

Figure 1A:
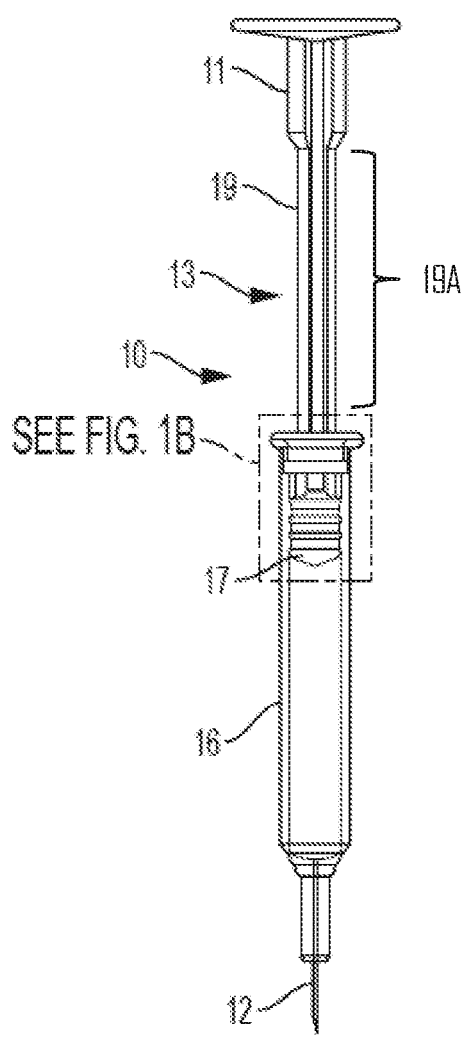
FIG. 1A is a front side elevational view of a syringe system in accordance with a first preferred embodiment of the present invention prior to dispensing medicament contained therein.

Certain terminology is used in the following description for convenience only and is not limiting. The words "right,"

"left," "lower," and "upper" designate directions in the drawings to which reference is made. The words "inwardly" and "outwardly" refer to directions toward and away from, respectively, the geometric center of the apparatus and designated parts thereof. The terminology includes the above-listed words, derivatives thereof, and words of similar import. Additionally, the words "a" and "an," as used in the claims and in the corresponding portions of the specification, mean "at least one."

Embodiments of the present invention preferably use an inlay containing an antenna pair and microcontroller capable of measuring capacitance across the antenna, combined with near-field communication (NFC) technology, to detect and report state changes in a syringe, auto-injector, pen injector, or other mechanical injection device, or container (e.g., a cartridge used in a self-injection device such as an auto-injector, patch injector, or the like). A microcontroller may measure changes in capacitance across the antenna due to movement of parts within the syringe or container. For example, and as described in more detail below, changes in the dielectric material (such as thickness or composition) within a syringe plunger located between probes of the antenna can result in measurable changes in the capacitance. Thus, such capacitance change data can be correlated to a change in state of the device, e.g., plunger position.

This state change information can easily be read and recorded by an external device, such as a smartphone or other NFC reading device, and can be tracked locally or via cloud-based servers to indicate drug usability (i.e., shelf life, prescription coordination, and the like), and injection frequency; and can record injection completion or partial completion, and advise the user as to the state of their injection system (complete or incomplete). One or more microcontrollers are preferably embedded into an inlay that can then be over-molded, thus encapsulating the technology into the body of the syringe or container. Alternately, the inlay can be adhered to the outer surface of the syringe or container, thus allowing interactive connectivity at a very low cost, without the need for an on-board power source. In some embodiments, the inlay may be omitted and the components thereof (e.g., antenna, microcontroller, and the like) can be embedded directly into portions of the syringe, such as the barrel, for example.

Figure 1B:
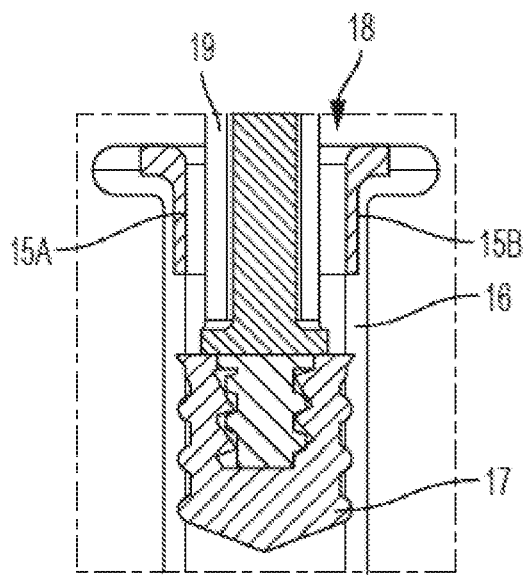
FIG. 1B is an enlarged, front side elevational cross-sectional view of a portion of the syringe system of FIG. 1A.

FIGS. 1A and 1B show a first embodiment of a syringe 10 that preferably includes a plunger 13, a barrel 16, and a needle 12 for administering medicine into a patient's body (not shown). Although a needle 12 is shown in FIG. 1A, other types of components for administering medicine can be used as well, such as a Luer connector or the like for connecting to an intravenous (IV) bag or other intermediate connector. The plunger 13 includes a shaft 19 and a piston 17 that can be used to expel the medicine (not shown) from the barrel 16. The shaft 19 extends longitudinally between a proximal end and a distal end, with the piston 17 being located at the distal end thereof. The barrel 16 has a proximal end, a distal end, and a cylindrical sidewall extending longitudinally between the proximal and distal ends, with the sidewall defining an internal volume containing the medicine (not shown) and in which the shaft 19 and piston 17 move to expel the medication. To assemble the syringe 10, the distal end of the plunger 13 (including the piston 17) can be inserted into the proximal end of the barrel 16 to enter the interior volume.

In the first embodiment, the shaft 19 includes a first section 19A having a first diameter and a second section 11 having a second diameter different from the first diameter. The second section 11 is preferably located between the first section and the proximal end of the plunger 13. In the embodiment shown in FIG. 1A, the second section 11 has a larger diameter than the first section of the shaft 19.

The syringe 10 is preferably provided with an inlay element 18 that can be attached to or inserted into the opening at the proximal end of the barrel 16. The inlay element 18, for example, can be mechanically inserted using a press-fit, threading, welding, adhesive, or other like methods in a cavity 1204 (FIG. 12) that can be molded, or insert-molded, into the barrel 16.

Figure 2:
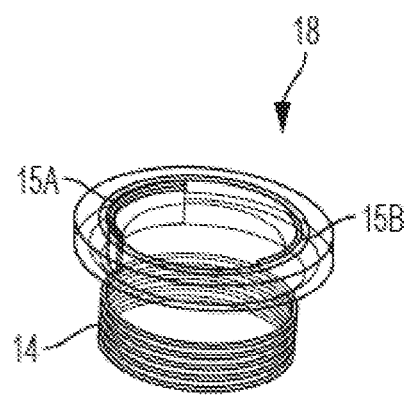
FIG. 2 is a perspective view of an inlay for use in the syringe system of FIG. 1A.
Figures 4A, 4B:
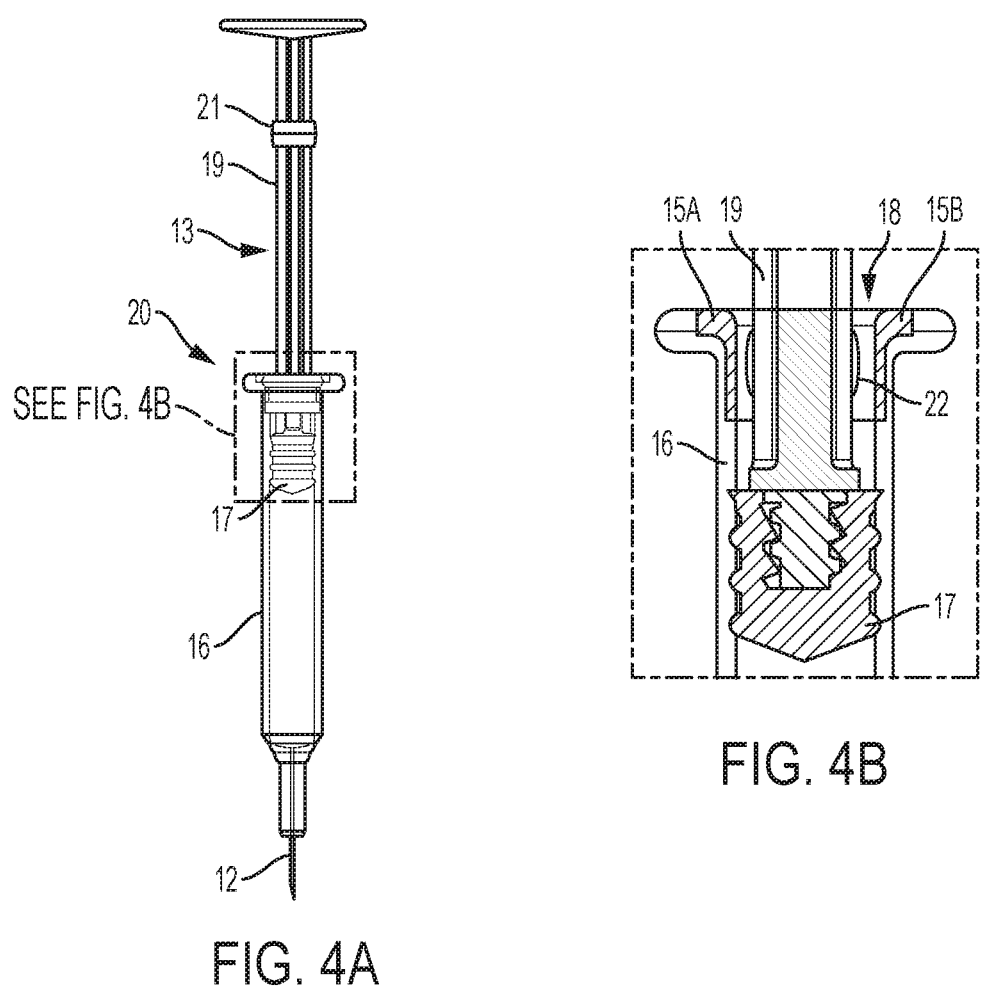
FIG. 4A is a front side elevational view of a syringe system in accordance with a second preferred embodiment of the present invention prior to dispensing medicament contained therein.
FIG. 4B is an enlarged, front side elevational cross-sectional view of a portion of the syringe system of FIG. 4A.
Figure 10A:
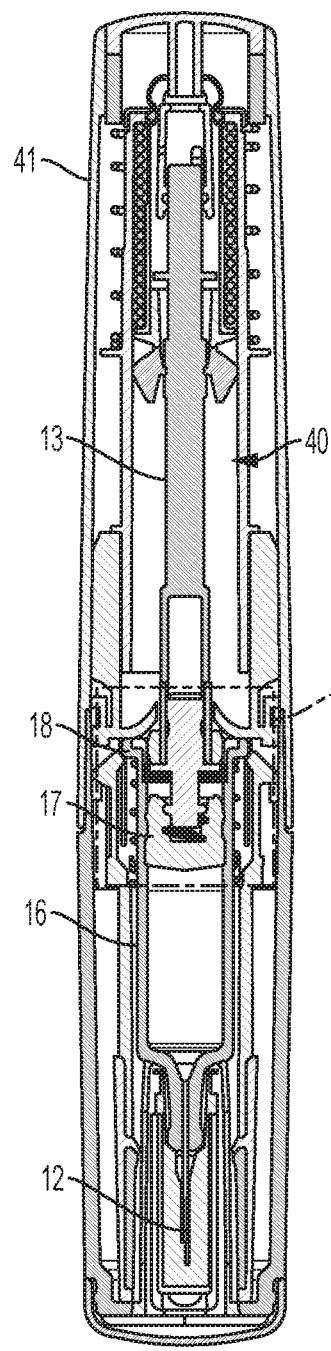
FIG. 10A is a front side elevational cross-sectional view of a syringe system embedded within an auto-injector, in accordance with a fourth preferred embodiment of the present invention before dispensing medicament therein.

FIG. 2 shows an embodiment of the inlay element 18, which can include an NFC antenna 14 and an antenna pair having first and second probes 15A, 15B: e.g., a positive probe 15A and a negative probe 15B. The first probe 15A and second probe 15B can be opposite to one another such that the interior volume of the barrel 16 is positioned radially between them. The two probes 15A, 15B can generate capacitance there-between that may be measured by a microcontroller 1201 (FIG. 12) in electrical communication with the first and second probes 15A, 15B and small enough to be embedded in the inlay element 18. Data related to the measured capacitance can be transmitted to a smart device 1202 (FIG. 12) via the NFC antenna 14. Although the first and second probes 15A, 15B and the NFC antenna 14 are shown as part of the inlay 18, these components may also be directly embedded or attached to the barrel 16. The inlays 18 shown in FIGS. 4B, 7A, and 10A are either the same or substantially similar to the inlay shown in FIG. 2.

The capacitance is influenced by a medium between the two probes 15A, 15B, e.g., the shaft 19 of the plunger 13 (or the absence thereof). In the exemplary embodiment shown in FIGS. 1A and 1B, before the medicine is injected, the first section 19A of the shaft 19 intersects the first and second probes 15A, 15B and, thus, a first capacitance value can be measured across the two probes 15A, 15B. When the injection is completed, as shown in FIGS. 3A and 3B, the second section 11 of the shaft 19, which in this embodiment has a larger diameter than the first section 19A, enters the space between the first and second probes 15A, 15B and, thus, a second capacitance value across the probes 15A, 15B may be detected by the microcontroller 1201. The second capacitance value increases or decreases relative to the first capacitance value due to the change in thickness of the medium between the first and second probes. Based on detection of the second capacitance value, the microcontroller 1201 preferably determines that an injection has been completed with the syringe 10, and may report this status to the smart device 1202, which may in turn report the information to the user.

The shaft 19 of the plunger 13 in this embodiment has a geometry such that it becomes thicker at the end of travel. However, the changes in thickness can also be reversed, such that a diameter of the second section 11 is smaller than the diameter of the first section 19A, for example. However, at a minimum, the shaft 19 should have at least two sections with different diameters, including one which is located at a portion of the shaft 19 that will only intersect the first and second probes at the end of injection to allow the microcontroller 1201 to determine that the injection has been completed. In some embodiments, the shaft 19 of the plunger 13 may have multiple diameters, which may provide sufficient resolution to enable detection of a location of the plunger 13 with respect to the barrel 16 between starting and ending positions. Such embodiments are particularly useful, for example, when multiple doses of the medicine are required to be administered. Such embodiments may also be useful to determine whether the plunger 13 has moved during shipping or the like.

FIGS. 4A-6B show a second embodiment of the disclosure. In this embodiment, the material composition of the plunger 13 is non-uniform in an axial direction along the shaft 19, while maintaining a constant diameter. For example, the shaft 19 may have a second section 21 with a different second material 21 embedded in it compared to the first material the first section 19A (FIG. 1A) of the shaft 19, i.e., the second material has a different dielectric constant than that of the first material. A change in material at the location of the inlay 18 will cause a change in the measured capacitance when the plunger 13 reaches the end of travel following an injection. This embodiment can also be expanded to include a metal or ceramic strip (not shown) or other material with a varying thickness along the length of the plunger 13, or many separate components having different dielectric constants stacked longitudinally along the plunger 13, so that an exact position of the plunger 13 can be measured by the microcontroller 1201. For example, the metal or ceramic strip can have a tapered shape and be embedded into the shaft 19 such that the overall diameter of the shaft 19 is constant along its axis, providing a continuous capacitance profile rather than discrete different capacitance values. Moreover, the shaft 19 can have a constant diameter and base material, but can be doped with, for example, metallic or ceramic particles, at different concentrations along its longitudinal axis.

Similar to the embodiment referenced in FIGS. 1A and 1B, the syringe 20 includes the plunger 13 with a shaft 19, the barrel 16 and the needle 12. An inlay element 18 may be inserted into the proximal end of the barrel 16. Different from the first embodiment, the relevant portion of the shaft 19 of the plunger 13 preferably has a first section 19A (FIG. 1A) of uniform thickness and material, but can include a second section 21 made of a second material different from the first material of the rest of the shaft 19 and particularly the first section 19A (FIG. 1A). The first and second materials also preferably have different dielectric constants. The second section 21 is disposed between the first section 19A (FIG. 1A) and the proximal end of the shaft 19 so as to intersect the first and second probes 15A, 15B when the syringe 20 has completed an injection. Accordingly, the capacitance measured across the first and second probes 15A, 15B by the microcontroller 1201 changes when the second section 21 intersects the probes 15A, 15B, as illustrated in FIGS. 6A and 6B. The microcontroller 1201 embedded in the inlay element 18 detects the completion of injection based on the change in capacitance and preferably communicates the status of the syringe 20 to the smart device 1202 via the NFC antenna 14. Additionally, a third section 22 made from a third material different from the first and materials can be disposed nearer to the piston 17, such that the syringe can detect three different positions of the plunger 13 based on three different measured capacitance values. In another embodiment, the second section 21 and the third section 22 can be moveable or fixed along the length of the plunger 13.

FIGS. 7A-9B show a third embodiment of the disclosure wherein the syringe 30 is enclosed within a manual self-injection device 31. As the plunger 13 moves toward the end of travel, the measured capacitance can change, and the state of the system can be transmitted to any NFC enabled device.

In FIGS. 7A-9B, the syringe 30, or at least a portion thereof, can be enclosed by or within a manual self-injection device 31. Similar to the embodiments shown and described above in FIGS. 1A-6B, the syringe 30 can include a plunger 13, a barrel 16, and a needle 12. An inlay element 18 can be inserted into the proximal end of the barrel 16; and a second section 32 of the plunger 13 can be provided at an appropriate position of the plunger 13 for detecting a change in capacitance between the first and second probes 15A, 15B of the inlay 18 when the syringe 30 completes an injection. When the injection is completed, the capacitance change can be detected by the microcontroller 1201 that communicates the status of the syringe 30 to a smart device 1202 via the NFC antenna 14. The second section 32 in the illustrated third embodiment may include a change in thickness of the shaft of the plunger 13 and/or a change in the material for changing the medium between the first and second probes 15A, 15B.

Figure 10B:
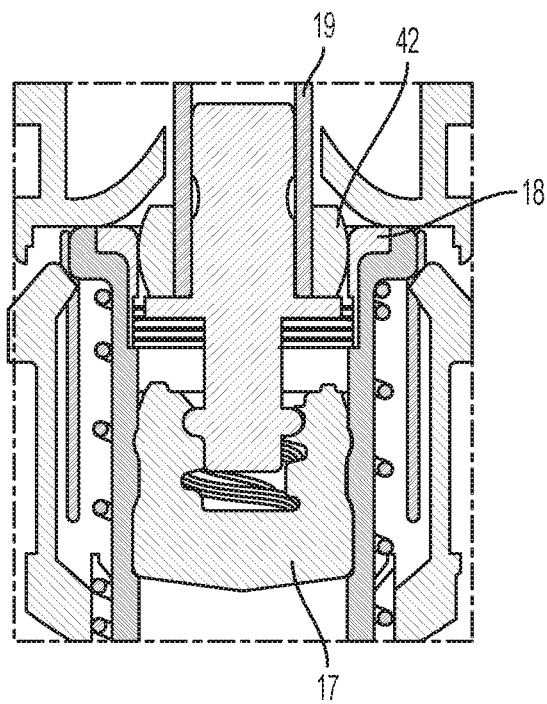
FIG. 10B is an enlarged, front side elevational cross-sectional view of a portion of the syringe system and auto-injector of FIG. 10A.
Figure 11:
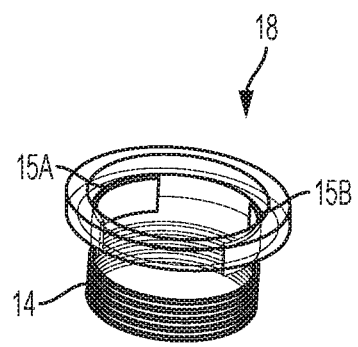
FIG. 11 is a perspective view of an inlay for use in the syringe system of FIG. 10A.

FIGS. 10A-11 show a fourth embodiment of the disclosure wherein the syringe 40 is implemented in an auto-injector 41. As with the other embodiments, the state and/or position of the plunger 13 can be detected by measured capacitance changes due to a change in plunger 13 material, thickness, or a combination of both. In addition to these documented embodiments, any drug containing vessel which uses a piston to dispense the drug may be equipped with this technology, such as a patch injector (not shown) with a telescoping plunger rod (not shown).

In FIGS. 10A-11, the syringe 40, or at least a portion thereof, is enclosed by or within an auto-injection device 41. Similar to the embodiments shown and described above in FIGS. 1A-6B, the syringe 40 can include a plunger 13, a barrel 16, and a needle 12. An inlay element 18 can be inserted into the proximal end of the barrel 16; and a second section 42 can be provided at an appropriate position of the plunger 13 for detecting a change in the capacitance between the first and second probes 15A, 15B of the inlay 18 when the syringe 40 completes an injection. When the injection is completed, the capacitance change is detected by a microcontroller 1201 that can communicate the status of the syringe 40 to a smart device 1202 via the NFC antenna 14. The second section 42 may include a change in thickness of the shaft of the plunger 13 and/or a change in the material for changing the medium between the first and second probes 15A, 15B.

Figure 12:
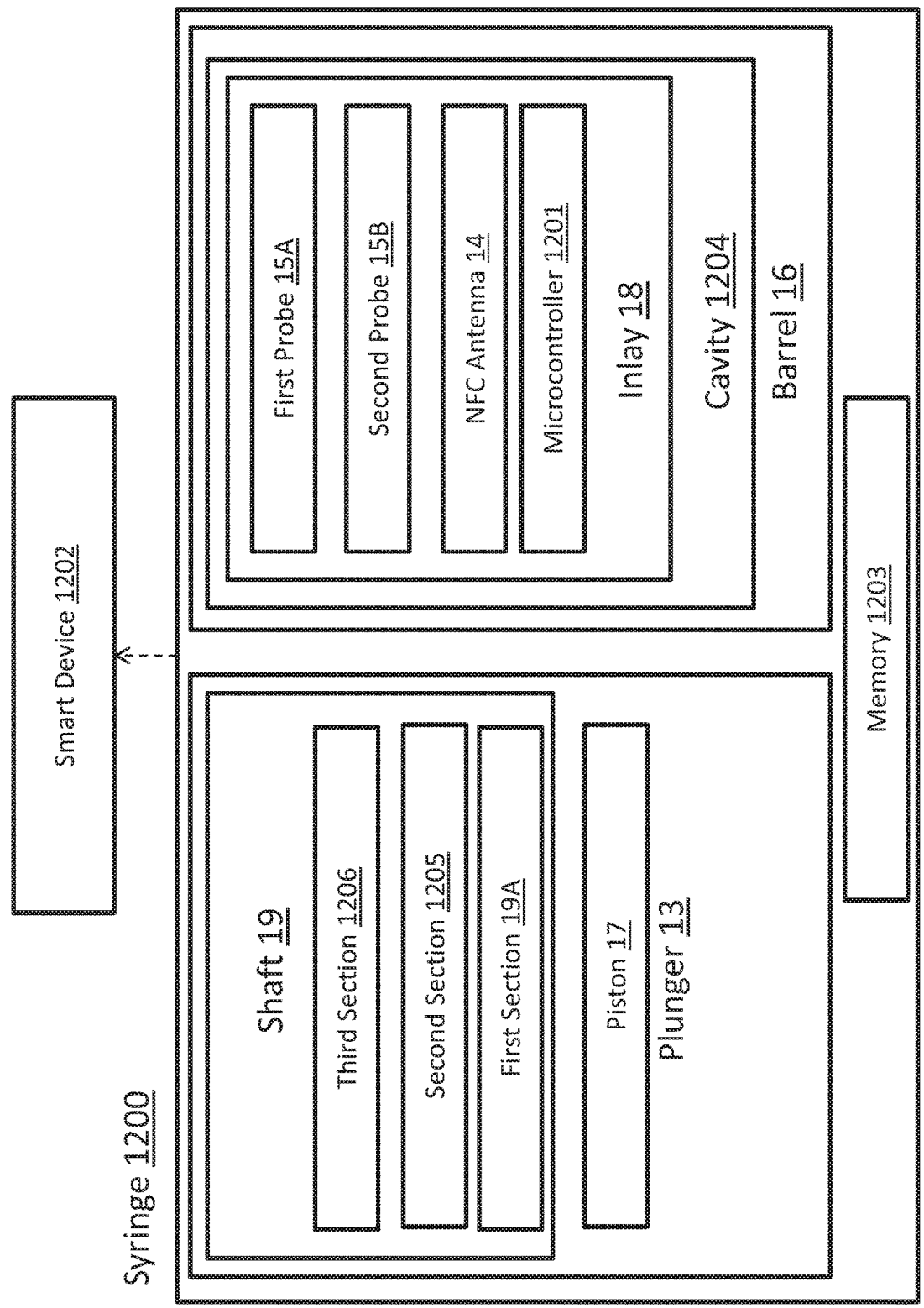
FIG. 12 is a schematic block diagram of a syringe system in accordance with certain preferred embodiments of the present invention.

FIG. 12 is a schematic block diagram depicting features of the syringe system 1200, in accordance with aspects described herein. The syringe 1200 preferably allows for communication of status information data (e.g., completion of an injection, plunger movement, and the like) to a smart device 1202, such as a smart phone, tablet, personal computer, or other digital medical system or the like, through NFC or other wireless protocols via an NFC antenna 14 or like wireless communication interface. Information regarding the plunger 13 position is preferably generated using capacitance detection based upon the interaction with the first section 19A of the shaft 19, second section 1205, and/or third section 1206 with the first probe 15A and second probe 15B of the inlay 18 disposed on the barrel 16, in conjunction with the microcontroller 1201.

The inlay 18 may be made from a flexible material and may include the following components embedded therein: the microcontroller 1201, such as the NXP NHS3100 or Cypress PSoC 6 32-bit internet-of-things microcontroller; the NFC antenna 14; and the first and second probes 15A, 15B to create the boundary of the capacitor. The flexible inlay 18 can be attached to or embedded within the syringe 1200 or delivery device so that the conductive elements surround a moving component with variable material properties which will create a measurable change in the capacitance of the system, measured by the microprocessor. Embodiments of the invention may be used to measure the current state of an injection device, for example if a prefilled syringe is in its open or unused state or if the plunger 13 has been depressed.

Additionally, the inlay 18 may take many forms and can be placed at any location along the barrel 16, and it may contain a larger or smaller NFC antenna 14 to either enable stronger communication or a smaller footprint, depending on the application. The inlay 18 can also be adhered, mechanically or chemically, to the outside of the syringe 1200, as the capacitance of the system can include the container material without changing the principal concept- that is, the measurement of the system between the first probe 15A and the second probe 15B The detected position or state change may be written to a memory 1203 to, for example, track any unintentional plunger movement or previous use of the syringe 1200. The memory 1203 may be mounted within the inlay 18, within the cavity 18, or within a suitable space along the barrel 16 of the syringe 1200. Additionally, the detection of the plunger 13 positions may allow a user to see when a dose was given and how much of the dose was given, ensuring adherence and proper drug dosing.

The microcontroller 1201 may determine if there has been a change in position of the plunger 13 by sampling at pre-determined intervals. In certain embodiments, the interval may be one second or shorter. If any change in plunger 13 position is detected, the microcontroller 1201 may record data and transmit to the connected smart device 1202 via the NFC antenna 14.

In certain aspects, the electronics used in this disclosure may be low-cost and small enough in scale to use on prefilled syringes and other injection devices. It may also be scaled to fit larger devices. The microcontroller 1201 may have a considerable power savings over previously created systems through the use of ultra-low boot cycles and a considerable 'inactive' duty cycle, which may minimize battery drain and idle time.

The main advantage of embodiments described herein is that the system can be configured to create a change in the measured capacitance during normal use of the device. The user does not have to activate any special features nor employ any additional steps other than the use of an NFC-enabled smart device 1202 to activate the microcontroller 1201 (via, e.g., "tapping" or passing the device near the syringe 1200).

Embodiments of the present invention can be employed across any device which uses a drug containment vessel that can be injection molded, which can then be used as a stand-alone device (i.e., a syringe), or inserted into a self-injection mechanism such as an auto-injector. Embodiments can also be applied to the outer diameter of a container or syringe, enabling glass containers to be used.

The technology can also be molded into the surrounding components of an auto-injector instead of the syringe itself, if this is feasible for design reasons. As the technology itself can optionally have no memory, it can also be re-usable, so it could be part of a re-usable system with replaceable drug cartridges or syringes, to detect current state of the device (ready-to-use, partially used or complete). A cloud-based data server can track the state over time, enabling a re-usable device to be connected to a patient, and their usage history captured.

These aspects are not meant to be limiting. For different injector systems, the positioning and size of the circuit may vary. It will be appreciated by persons skilled in the art that the present disclosure is not limited by what has been particularly shown and described hereinabove. Rather the scope of the present disclosure includes both combinations and sub-combinations of various features described hereinabove as well as modifications and variations which would occur to persons skilled in the art upon reading the foregoing description and which are not in the prior art.

What is claimed is:

1. A syringe, comprising:
    a plunger having a piston at a distal end and a shaft extending longitudinally between a proximal end and the distal end, the shaft including:
        a first section having a first diameter, and
        a second section having a second diameter different from the first diameter, the second section being disposed between the first section and the proximal end of the plunger;
    a barrel having a cylindrical sidewall extending longitudinally, the sidewall defining an internal volume, the distal end of the plunger being inserted into a proximal end of the barrel and being movable within the internal volume with respect to the barrel in a longitudinal direction;
    a first probe and a second probe embedded or attached to the barrel adjacent the proximal end of the barrel, the first and second probes being positioned opposite to one another such that the internal volume of the barrel is radially between the first and second probes; and
    a microcontroller disposed on the barrel and in electrical communication with the first and second probes, the microcontroller being configured to:
        measure a capacitance between the first and second probes, the measured capacitance having a first capacitance value when the first section of the shaft is between the first and second probes and a second capacitance value when the second section of the shaft is between the first and second probes, the second capacitance valve being different from the first capacitance value, and
        generate a signal indicating that an injection has been completed when the second section of the shaft is between the first and second probes based on the second capacitance value being measured.

2. The syringe of claim 1, further comprising a near-field communication (NFC) antenna disposed on the barrel and communicatively coupled to the microcontroller, the microcontroller being further configured to transmit data related to the injection to an external device via the NFC antenna.

3. The syringe of claim 1, further comprising a memory disposed on the barrel and configured to store data related to capacitance measurements made by the microcontroller.

4. The syringe of claim 1, wherein the second diameter is larger than the first diameter.

5. The syringe of claim 1, wherein at least a portion of each of the plunger and the barrel are enclosed within one of a manual self-injection device or an auto-injection device.

6. The syringe of claim 1, further comprising an inlay attached to the barrel, wherein the inlay includes the first and second probes and the microcontroller.

7. The syringe of claim 6, wherein the inlay is molded into the barrel.

8. The syringe of claim 1, wherein the first section is made from a first material having a first dialectic constant, and the second section is made from a second material having a second dialectic constant different from the first dialectic constant.

9. The syringe of claim 8,
wherein the plunger further includes a third section made from a third material different from the first and second materials, the third section being disposed between the first and second sections, the measured capacitance having a third capacitance value different from the first and second capacitance values when the third section is between the first and second probes, and wherein the microcontroller is configured to determine a position of the plunger based on the measured capacitance.

10. The syringe of claim 1, wherein the plunger contacts an inner surface of the barrel.

11. The syringe of claim 1, further comprising a medicine disposed in the internal volume.

12. The syringe of claim 1, further comprising a needle attached to a distal end of the barrel.

13. A system comprising:
the syringe of claim 1; and
a device in communication with the microcontroller of the syringe.

14. The syringe of claim 1, wherein the first probe is positive and the second probe is negative.

15. The syringe of claim 1, wherein the shaft includes a third section having a third diameter, and the measured capacitance has a third capacitance value when the third section of the shaft is between the first and second probes.

16. The syringe of claim 15, wherein the microcontroller is configured to determine that a second injection has been completed when the third capacitance value is measured, and the injection and the second injection are doses.

17. The syringe of claim 2, wherein the NFC antenna is a coil.

18. The syringe of claim 6, wherein the inlay is adhered to an outer surface of the barrel.

19. A manual self-injector comprising the syringe of claim 1.

20. An auto-injector comprising the syringe of claim 1.

21. A patch injector comprising:
the syringe of claim 1; and
a telescoping plunger rod.

22. A method of using the syringe of claim 1, the method comprising:
measuring, by the microcontroller, the first capacitance value when the first section of the plunger is disposed between the first and second probes;
measuring, by the microcontroller, the second capacitance value when the second section of the plunger is disposed between the first and second probes; and
determining, by the microcontroller, that the injection has been completed when the second capacitance value has been measured.

23. The method of claim 22, further comprising transmitting, by the microcontroller via a near-field communication antenna, data regarding the injection to a smart device or a cloud-based server.

24. The method of claim 22, further comprising:
measuring, by the microcontroller, a third capacitance value between the first and second probes when a third section of the plunger between the first and second sections is disposed between the first and second probes, the third capacitance value being different than the first and second capacitance values; and
determining, by the microcontroller, a position of the plunger relative to the barrel based on the first and second probes measuring the third capacitance values.

25. The method of claim 22, further comprising storing, by the microcontroller, data regarding the injection in a memory disposed on the barrel.

* * * * *